(12) United States Patent
Stillwagon

(10) Patent No.: US 8,079,947 B2
(45) Date of Patent: Dec. 20, 2011

(54) INTERNAL RADIATION THERAPY DEVICE

(76) Inventor: Gary B. Stillwagon, Atlanta, GA (US)

( * ) Notice: Subject to any disclaimer, the term of this patent is extended or adjusted under 35 U.S.C. 154(b) by 972 days.

(21) Appl. No.: 12/072,075

(22) Filed: Feb. 22, 2008

(65) Prior Publication Data
US 2008/0146863 A1 Jun. 19, 2008

Related U.S. Application Data

(63) Continuation-in-part of application No. 10/899,890, filed on Jul. 26, 2004, now abandoned.

(51) Int. Cl.
*A61N 5/00* (2006.01)
(52) U.S. Cl. ............................................................ 600/6
(58) Field of Classification Search .................. 600/1–8, 600/38–41; 604/358, 385.01, 385.03, 392
See application file for complete search history.

(56) References Cited

U.S. PATENT DOCUMENTS

| 3,750,653 | A | * | 8/1973 | Simon | 600/6 |
| 6,482,142 | B1 | * | 11/2002 | Winkler et al. | 600/3 |
| 6,491,618 | B1 | * | 12/2002 | Ganz | 600/3 |
| 6,607,477 | B1 | * | 8/2003 | Longton et al. | 600/3 |
| 7,147,627 | B2 | * | 12/2006 | Kim et al. | 604/327 |
| 7,338,430 | B2 | * | 3/2008 | Lim et al. | 600/7 |

* cited by examiner

*Primary Examiner* — John Lacyk
(74) *Attorney, Agent, or Firm* — Rodgers & Rodgers

(57) ABSTRACT

An internal radiation therapy device including concentric inner and outer tubes with the inner tube being inflexible and an isotope tube extending into the inner tube and being filled with a radioisotope through an isotope tube or x-ray source and the outer flexible tube filled through a filler tube with a material having radiation characteristics similar to human tissue.

6 Claims, 2 Drawing Sheets

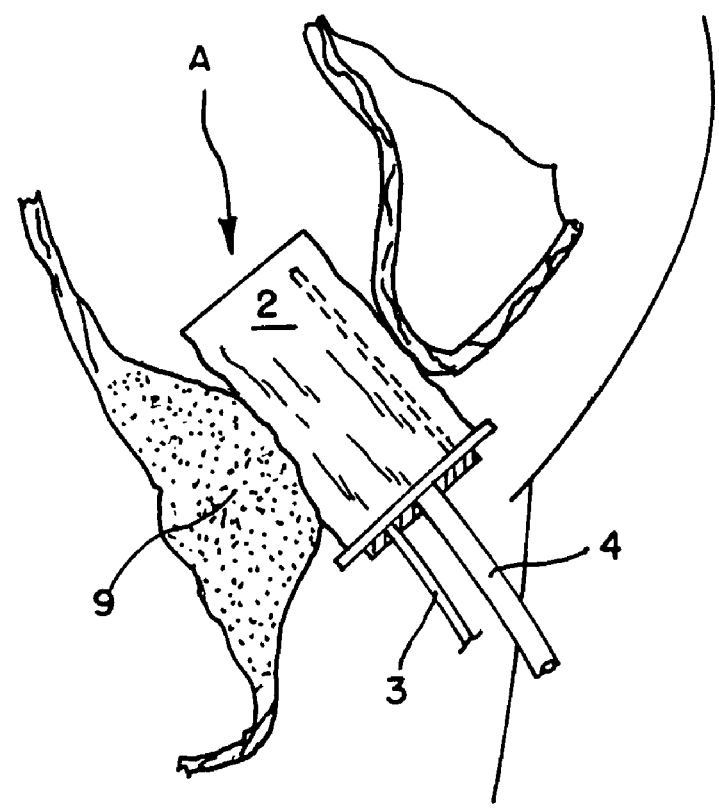
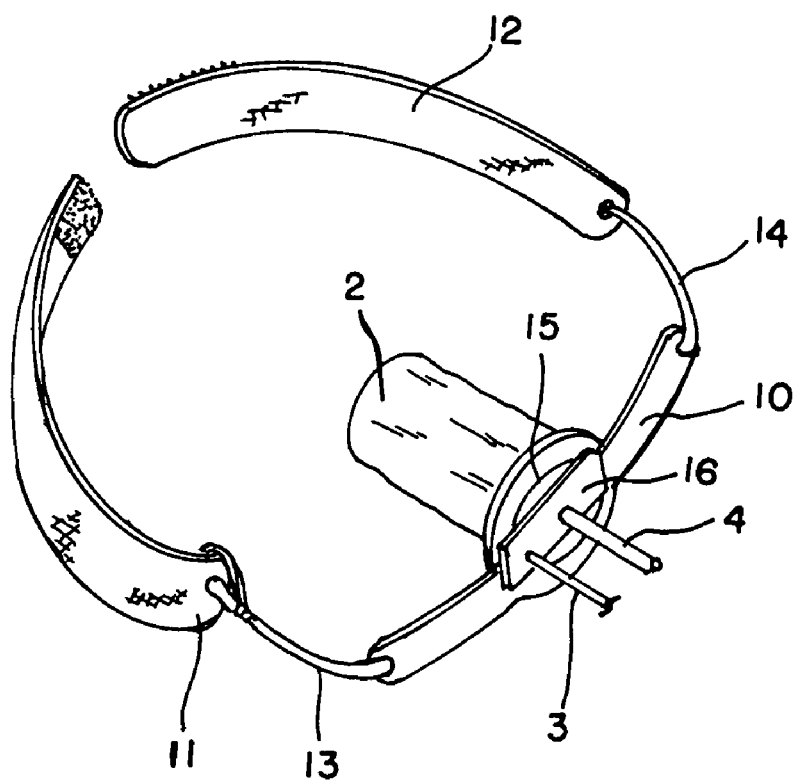
FIG. 4
FIG. 5

INTERNAL RADIATION THERAPY DEVICE

This is a continuation-in-part of patent application Ser. No. 10/899,890 filed Jul. 26, 2004 now abandoned.

BACKGROUND OF THE INVENTION

In the field of radiation therapy for low-lying bowel cancers, there are several methods that historically have been utilized to irradiate the distal gastrointestinal tract. One method includes an external beam. Other methods are essentially internal, such as brachytherapy, which are often difficult and cumbersome in actual practice.

In general, radiotherapy, as applied to the distal gastrointestinal tract, is used in preoperative, postoperative, definitive and palliative modes.

In the preoperative mode, radiotherapy can reduce the extent of the cancer so as to facilitate surgical resections.

In the postoperative mode, radiotherapy is utilized after surgical resection when pathologic findings warrant the use of radiotherapy.

In the definitive mode, radiation therapy is used widely in connection with anal cancers, unresectable rectal cancers, and resectable recto-sigmoid cancers which occur in patients who are medically not suited for surgery or who refuse surgery.

Palliative uses of radiation therapy include addressing such quality of life issues as stoppage of bleeding, etc.

Known problems which are encountered with the use of external radiation therapy include the toxicity caused by bowel irradiation and the relative long duration over which treatment must be administered in order to achieve reasonable benefits versus risks.

With respect to internal radiation therapy, problems often arise relating to the difficulty of implementing the treatment and the lack of a cohesive procedure for incorporation into an overall health management program.

In addition, organ preservation is sometimes hindered by the lack of the convenient availability of radiation therapy facilities or the significant time commitment needed to implement the radiotherapy program. This problem was especially apparent in connection with breast cancer in terms of breast conservation treatment.

BRIEF SUMMARY OF THE INVENTION

An internal radiation therapy device includes a flexible outer tube and a concentrically disposed inflexible inner tube with a filler tube extending from the outer tube for the purpose of injecting a material having characteristics similar to that of human tissue and an isotope tube extending into the inner tube for the purpose of introducing the radioisotope into the isotope tube. A curved lead shield is disposed within a similarly curved slot formed in the inner tube for the protection of tissue disposed remotely from the cancer being treated.

BRIEF DESCRIPTION OF THE SEVERAL VIEWS OF THE DRAWINGS

In the drawings:

FIG. 4 is an enlarged side view showing the device used in connection with a cancerous tumor; and FIG. 5 is a perspective view of the device and support strap.

DETAILED DESCRIPTION OF THE INVENTION

Figure 1:
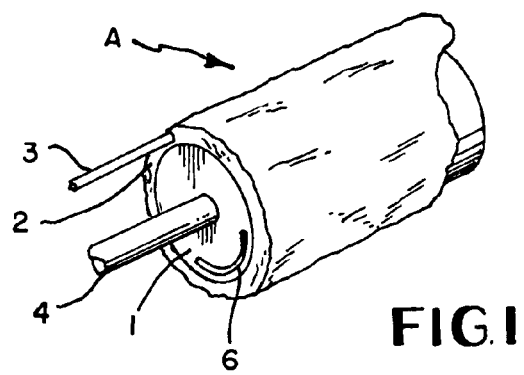
FIG. 1 is a perspective view of the internal radiation therapy device according to this invention.
Figure 2:
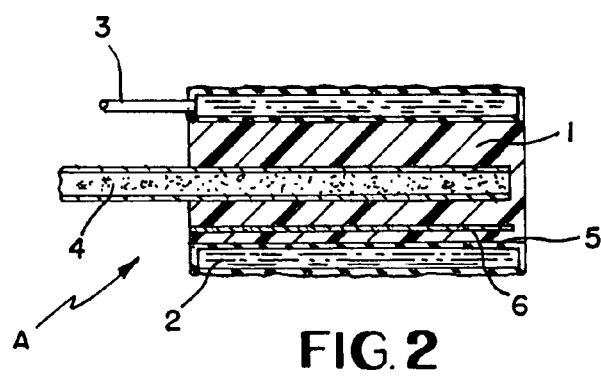
FIG. 2 is a cross-sectional view of the device shown in FIG. 1.

In the drawings and with particular reference to FIGS. 1 and 2, the internal radiation therapy device, according to this invention, is generally identified by the letter A and includes a pair of concentric tubes including inner inflexible plastic tube 1 and outer flexible tube 2. Outer flexible tube 2 is filled by means of filler tube 3 with a material having radiation characteristics similar to that of human tissue. One example of such material is water. Radioisotope is introduced into inflexible inner tube 1 by means of isotope tube 4 and is retained within isotope tube 4. In order to shield the portion of the rectum disposed opposite from the cancer, curved lead shield 5 is inserted into curved slot 6 formed in inner tube 1.

Figure 3:
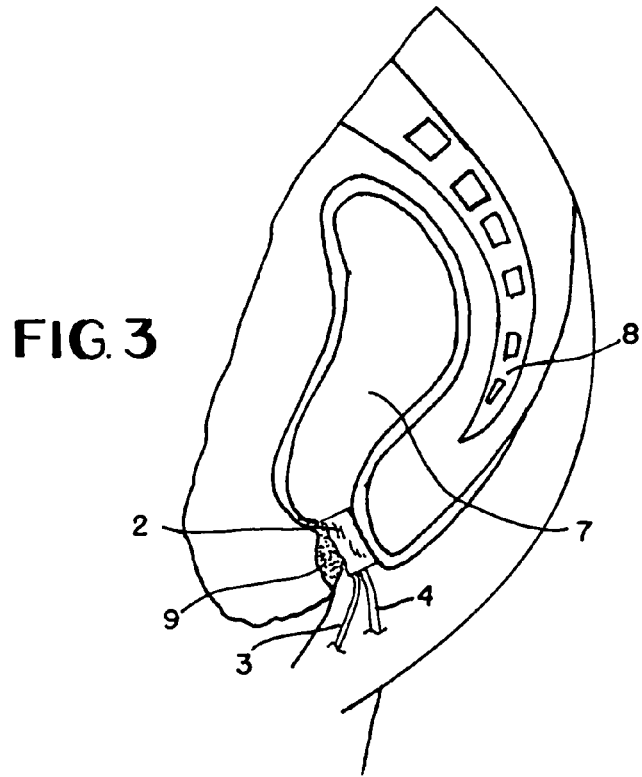
FIG. 3 is a side view of the device in place in the rectum.

In FIG. 3, the environment in which the internal radiation therapy device is utilized is shown and includes rectum 7, sacrum 8 and tumor 9 or tumor volume, if the tumor has been removed for post-operative treatment. In practice, internal radiation therapy device A is inserted into the rectum to a position whereby tumor 9 is generally centered adjacent to the device. Since fluid-filled outer tube 2 is flexible in nature, as the device is placed in the desired position, outer tube 2 will conform generally to the surface characteristics of tumor 9. Isotope tube 4 is then interconnected to an appropriate apparatus for introduction of the radioisotope at a high dose rate. Also, the device is manufactured of a size in which the diameter of the tube is variable depending on the requirements of the source of the radiation and the patient's body characteristics.

Following administration of the desired radioisotope dosage, fluid is removed from outer tube 2 through filler tube 3 such that the device is deflated to a degree and conveniently removed. Additional treatments are then administered pursuant to the term of the radiotherapy program which can involve a week or longer in duration depending on the dose distribution, treatment goal and whether or not treatment is administered in combination with other types of treatments.

So that the internal radiation therapy device, according to this invention, does not move during treatment, a belt apparatus is employed, as shown in FIG. 5, and includes elongated bracket 10 with straps 11 and 12 attached to the ends thereof, respectively, by means of hooks 13 and 14. The free ends of straps 11 and 12 are secured together by any known means such as Velcro and the like. In operation, bracket 10 is placed against the outer end of the device with filler tube 3 and isotope tube 4 extending through aperture 15. Flange 16 extends across aperture 15 and prevents the device from extending beyond bracket 10. Therefore, during treatment, the device is held securely in place by means of interconnected straps 11 and 12 extending around the patient's body.

Therefore, by this invention, the utilization of the high dose rate technique allows a high dose per treatment to be given safely which shortens the overall time period, in days, during which the treatment regimen is administered. By comparison, the conventional lower dose per treatment method used in external beam radiotherapy extends the treatment over a longer period of time.

The invention claimed is:

1. An internal radiation therapy device comprising an inner tube, an outer flexible tube, an isotope tube extending from an end of said inner tub; a filler tube extending from the corresponding end of said outer tube, said tubes being concentrically disposed, a bracket disposed in abutting demountable relation with said ends of said inner and outer tubes, a pair of straps attached respectively to opposite ends of said bracket, an aperture formed in said bracket, said isotope tube and said filler tube extending through said aperture, and a flange extending across said aperture.

2. A device according to claim 1 wherein said inner tube is inflexible.

3. A device according to claim 1 wherein said outer tube is filled through said filler tube with a material having radiation characteristics similar to human tissue.

4. A device according to claim 1 wherein radioisotope is introduced into said inner tube by means of said isotope tube.

5. A device according to claim 1 wherein a slot is formed in said inner tube and a lead shield is disposed in said slot.

6. A device according to claim 5 wherein said slot and said shield are curved.

* * * * *